United States Patent
Bristow

(10) Patent No.: US 10,336,714 B2
(45) Date of Patent: *Jul. 2, 2019

(54) PROCESS FOR PREPARING A NOVEL CRYSTALLINE FORM OF METSULFURON-METHYL AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: Rotam Agrochem International Co. Ltd., Chai Wan (HK)

( * ) Notice: Subject to any disclaimer, the term of this patent is extended or adjusted under 35 U.S.C. 154(b) by 0 days.

This patent is subject to a terminal disclaimer.

(21) Appl. No.: 14/926,058

(22) Filed: Oct. 29, 2015

(65) Prior Publication Data

US 2017/0121293 A1    May 4, 2017

(51) Int. Cl.
| | | |
|---|---|---|
| *A01N 47/36* | (2006.01) | |
| *A01N 25/12* | (2006.01) | |
| *A01N 25/14* | (2006.01) | |
| *C07D 251/16* | (2006.01) | |
| *C07D 251/42* | (2006.01) | |

(52) U.S. Cl.
CPC ........... *C07D 251/42* (2013.01); *A01N 25/12* (2013.01); *A01N 47/36* (2013.01); *C07D 251/16* (2013.01); *C07B 2200/13* (2013.01)

(58) Field of Classification Search
CPC .............................. A01N 47/36; C07D 251/16
See application file for complete search history.

(56) References Cited

U.S. PATENT DOCUMENTS

| 4,954,628 | A | * | 9/1990 | Besenyei | ............. | C07D 521/00 544/197 |
| 5,550,238 | A | * | 8/1996 | Chiang | ................. | C07D 521/00 544/206 |
| 2015/0031877 | A1 | * | 1/2015 | Hiratsuka | .............. | A01N 43/84 544/105 |
| 2017/0118986 | A1 | * | 5/2017 | Bristow | ................. | A01N 47/36 |

FOREIGN PATENT DOCUMENTS

| EP | 0030138 A1 | 6/1981 |
| EP | 0318276 A1 | 5/1989 |

OTHER PUBLICATIONS

HCAPLUS abstract 1999:261209 (1999).*
Roberts, R.M. et al. Modern Experimental Organic Chemistry. Holt, Rinehart and Winston, New York, 1979, pp. 49-58.*
McClurg, R.B., "X-Ray Powder Diffraction (XRPD) to Describe Crystal Forms," Publication of SSCI an Aptuit Company, Jul. 9, 2008, pp. 1-23.*
International Search Report and Written Opinion regarding PCT/CN2016/098340 dated Nov. 30, 2016.
Li, Zhixiang A Purify Method for Metsulfuron-Methyl Pesticide Science for Administration Aug. 15, 1998 (Aug. 15, 1998) No. 3 vol. 19 ISSN: 1002-5480 p. 9.
Hu, Xianwen et al. Purification, Characterization and Determination of Metsulfuron. Hubei Agricultural Sciences Sep. 30, 2003 (Sep. 30, 2003) No. 5 ISSN: 0439-8114 pp. 51-52.
Caira, Mino R. Crystalline Polymorphism of Organic Compounds Topics in Current Chemistry Jan. 1, 1998 (Jan. 1, 1998) vol. 198 ISSN: 0340-102 pp. 163-208.

* cited by examiner

*Primary Examiner* — John Pak
(74) *Attorney, Agent, or Firm* — Dickinson Wright PLLC

(57) ABSTRACT

A crystalline form of metsulfuron-methyl of formula (I), the crystal preparation process, the analyses of the crystal through various analytical methods and using the crystal to prepare stable agrochemical formulation. The invention also describes the use of various solvents towards the crystalline form preparation conditions.

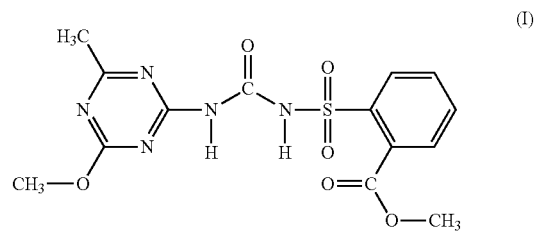

9 Claims, 4 Drawing Sheets

PROCESS FOR PREPARING A NOVEL CRYSTALLINE FORM OF METSULFURON-METHYL AND USE OF THE SAME

BACKGROUND

Field

The present disclosure relates to a crystalline form of methyl 2-(4-methoxy-6-methyl-1,3,5-triazin-2-ylcarbamoylsulfamoyl)benzoate (metsulfuron-methyl), to its preparation processes and to its use in agrochemical preparations.

Description of Related Art

Metsulfuron-methyl, i.e., methyl 2-[[[[(4-methoxy-6-methyl-1,3,5-triazin-2-yl)amino]carbonyl]amino]sulfonyl]benzoate is a member of the sulfonylurea group of chemicals and used as herbicide. Metsulfuron-methyl is a residual sulfonylurea herbicide against broadleaved weed and is one of the most important in its class for use in the cereals sector, where it competes against broad-spectrum commodity products. Whilst metsulfuron-methyl sales are now stable, it is still important in cereal weed control strategies and is used in premixes, such as with flupyrsulfuron under the brand name LEXUS® XPE, and with carfentrazone under the brand name ALLY EXPRESS®. It is a leading product in the U.S. cereal herbicide sector. Metsulfuron-methyl is also used to control woody plants and annual and perennial weeds in non-crop applications in the U.S. under the brand name ESCORT®, and is used in rangeland under the brand name CIMARRON®.

Metsulfuron-methyl has molecular formula of $C_{14}H_{15}N_5O_6S$. Its chemical structure is

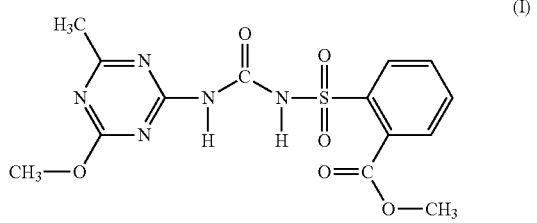 [SMILES: COC(=O)c1ccccc1S(=O)(=O)NC(=O)Nc1nc(C)nc(OC)n1]

(I)

The commercially available metsulfuron-methyl, which is usually manufactured by the process described in EP 0318276, is present in an amorphous state having a melting point of about 158° C.

SUMMARY

It has been found that metsulfuron-methyl in amorphous state is highly viscous when dissolved, which is not suitable for use in compositions or formulations where spray equipment cleanout is important, since metsulfuron-methyl residues tend to remain in the spray equipment after spraying is completed, and the spray equipment is prepared for other use. Adequate cleanout may require a rinsing procedure that is time-consuming and results in a wastewater disposal problem. Therefore, a novel form of metsulfuron-methyl with improvement in solubility and viscosity is highly demanding.

In an embodiment of the invention, a crystalline form of metsulfuron-methyl, hereinafter "crystalline modification I", has been found which, when used in spray equipment, provides improved spray equipment clean-out properties.

Accordingly, in one embodiment, the invention provides a novel crystalline form of metsulfuron-methyl, termed "crystalline modification I", and a process for its preparation as well as methods for its use in agrochemical compositions. The novel crystalline modification I has been found to have increased solubility, decreased viscosity and improved spray equipment clean-out properties.

Accordingly, in another embodiment, the invention also provides compositions for controlling undesirable weeds comprising applying the crystalline modification I of metsulfuron-methyl, either on its own, as a mixture with auxiliaries and carriers, or as a mixture with other active compounds.

BRIEF DESCRIPTION OF DRAWINGS

Various aspects of the invention can be more clearly understood by reference to the drawings, which are described below, and are intended to be illustrative, not limiting, of the invention.

DETAILED DESCRIPTION OF SPECIFIC EMBODIMENTS

The embodiments and aspects of the invention disclosed herein can be more clearly understood by the following detailed description of specific embodiments and examples, which are intended to illustrate, but not limit, the scope of the appended claims.

It has been found that the present crystalline modification I of metsulfuron-methyl has a significant increase in its solubility and a significant decrease in its viscosity, which significantly reduces the residue contamination and improves spray equipment clean-out properties. In addition, it has been found that the crystalline modification I of metsulfuron-methyl is easier to comminute or grind, compared to amorphous metsulfuron-methyl prepared in accordance with the disclosure of EP 0318276. This allows the crystalline modification I to be more easily included in the preparation of commercial formulations such as suspension concentrates (SC), oil-based suspension concentrates (OD), water-dispersible granules (WG) and water-soluble granules (SG). Hence, it is possible to prepare any formulations of metsulfuron-methyl in crystal modification I, as will be disclosed in more detail hereinafter.

By virtue of its high solubility and low viscosity, the crystalline modification I of metsulfuron-methyl is highly suitable for preparing compositions for controlling undesirable weeds.

According to an embodiment of the invention, a crystalline modification I of metsulfuron-methyl is provided, exhibiting at least 3 of the following reflexes as 2θ values in an X-ray powder diffractogram recorded using Cu-Kα radiation at 25° C.:

2θ=6.28±0.2 (1)

2θ=12.61±0.2 (2)

2θ=13.50±0.2 (3)

2θ=16.59±0.2 (4)

2θ=17.66±0.2 (5)

2θ=19.70±0.2 (6)

2θ=21.63±0.2 (7)

2θ=21.84±0.2 (8)

2θ=23.22±0.2 (9)

2θ=24.21±0.2 (10)

2θ=27.25±0.2 (11)

2θ=27.98±0.2 (12)

2θ=29.25±0.2 (13).

Figure 2:
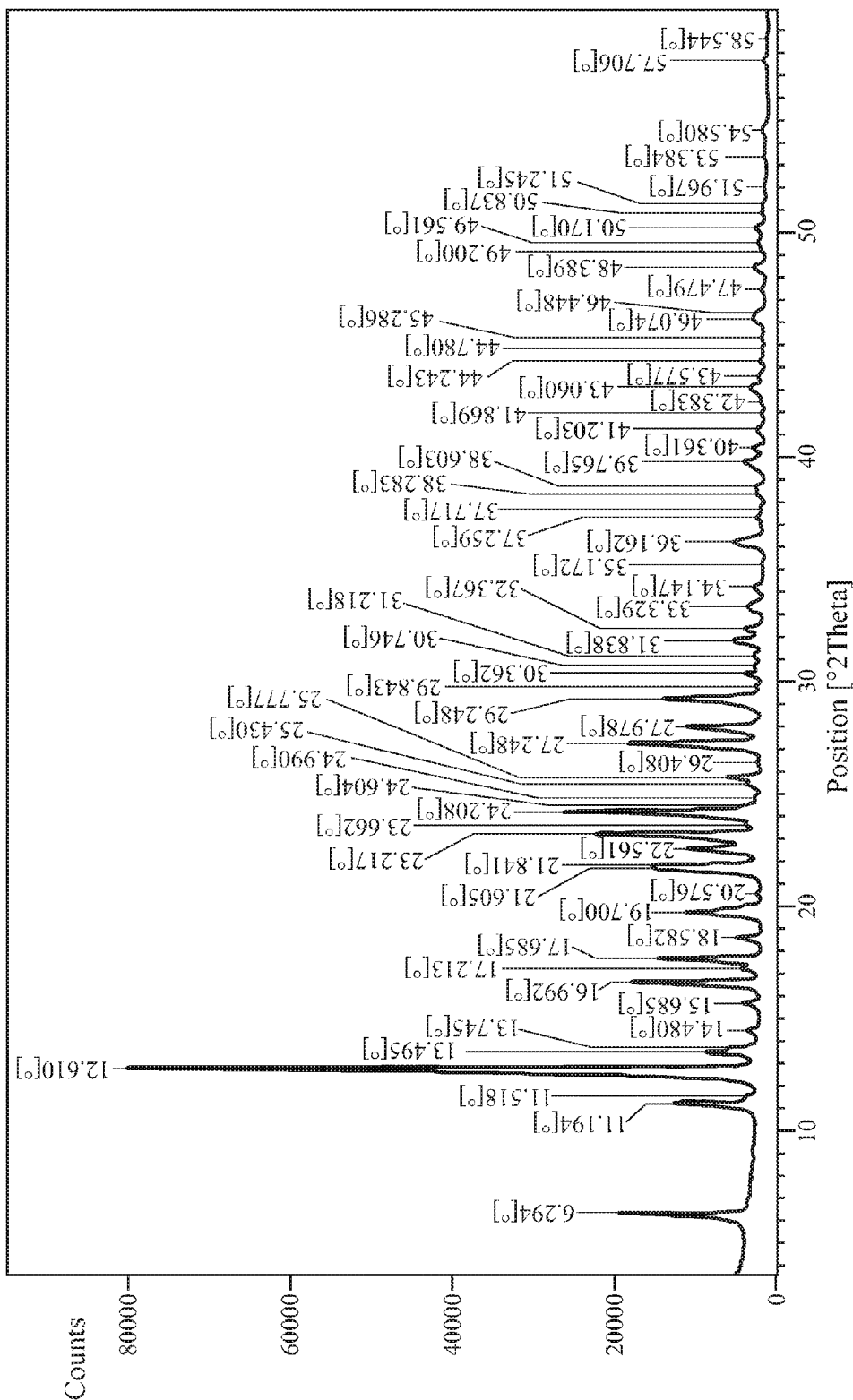
FIG. 2 is a graph showing the results of an X-ray powder diffractogram (XRD) of crystalline modification I of metsulfuron-methyl, according to an embodiment of the invention.

More particularly, the crystalline modification I of metsulfuron-methyl of the invention is characterized by an X-ray powder diffractogram having at least three of the reflexes indicated above. Preferably, the crystalline modification I is one having at least four of the aforementioned reflexes, more preferably at least five, six, seven, or eight of said reflexes. An X-ray powder diffractogram of an embodiment of the crystalline modification I of metsulfuron-methyl is shown in FIG. 2, which will be described in detail hereinafter.

According to a preferred embodiment, the crystalline modification I exhibits at least 3, 4, or 5, or all of the reflexes from the following:

2θ=6.28±0.2 (1)

2θ=12.61±0.2 (2)

2θ=16.59±0.2 (4)

2θ=23.22±0.2 (9)

2θ=24.21±0.2 (10)

2θ=27.25±0.2 (11).

Figure 1:
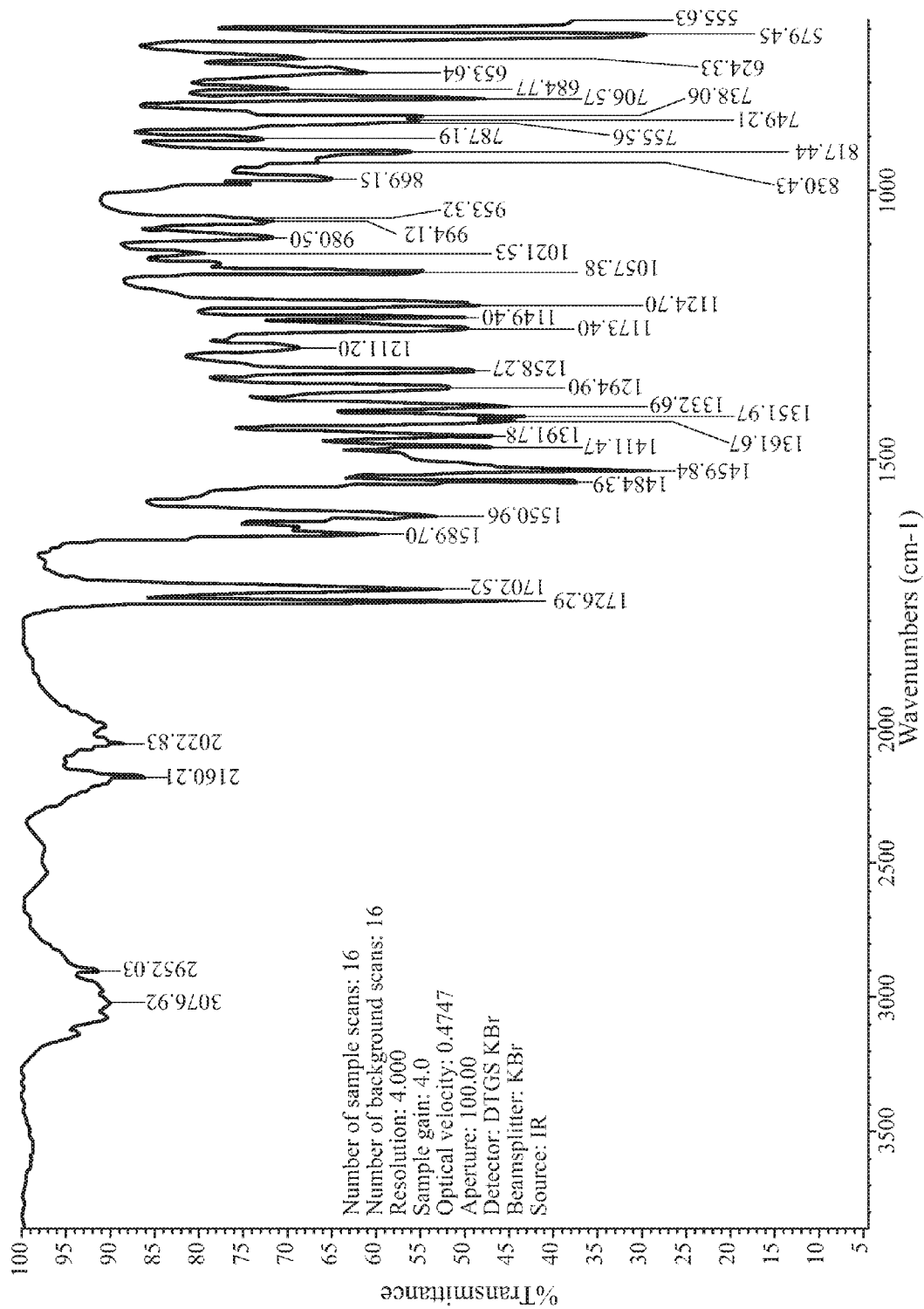
FIG. 1 is a graph showing the results of an infrared (IR) spectrograph of crystalline modification I of metsulfuron-methyl, according to an embodiment of the invention.

Further to X-ray diffraction analysis, the crystalline modification I of metsulfuron-methyl according to an embodiment can also be characterized by IR spectroscopy. The IR spectrum was measured with the resolution of 4 cm$^{-1}$ and with the number of scans of 16 for the purified sample. The IR spectrum of crystalline modification I of metsulfuron-methyl can be identified by its characteristic functional group vibrations (characteristic bands) at 3076.92, 2952.03, 2160.21, 2022.83, 1726.29 and 1702.52 cm$^{-1}$ as shown in FIG. 1.

All IR spectra were obtained using the following acquisition parameters:

| | |
|---|---|
| FT-IR spectrometer | Bruker Tensor37 |
| Diamond ATR unit | from Specac |
| Wavelength range | 550-4000 cm$^{-1}$ |
| Resolution | 4 cm$^{-1}$ |
| Number of scans | 16 |

Figure 3:
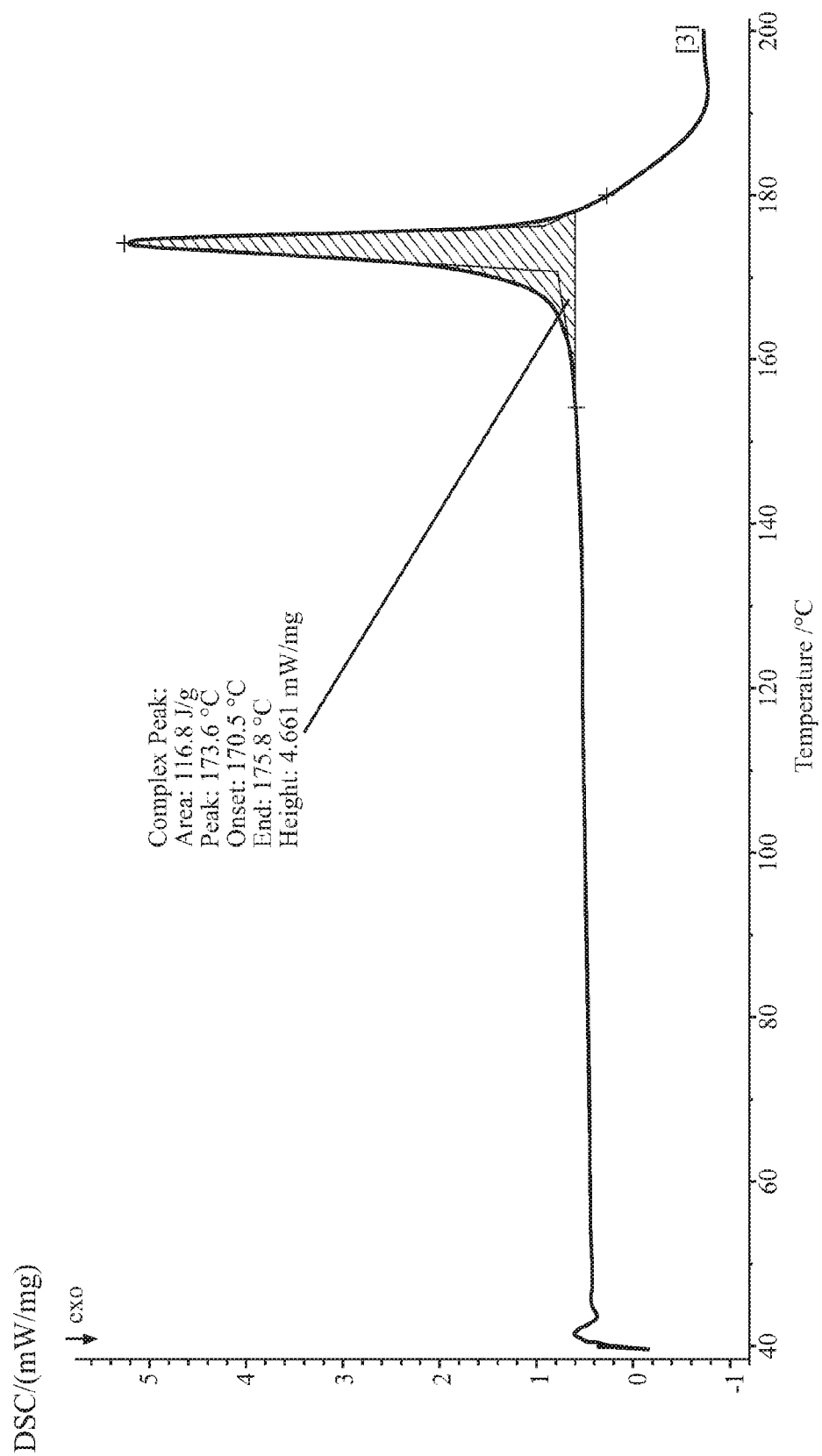
FIG. 3 is a Differential Scanning calorimetry (DSC) thermogram of crystal modification I of metsulfuron-methyl, according to an embodiment of the invention.

The crystalline modification I of metsulfuron-methyl according to the invention may be further characterized by differential scanning calorimetry (DSC) (FIG. 3). An endothermic melting peak with onset at 170.5° C. and peak maximum at 173.6° C. is shown in FIG. 3.

Methods for preparing amorphous metsulfuron-methyl are well known in the art. Amorphous metsulfuron-methyl is manufactured and available on a commercial scale. A particularly suitable method for preparing amorphous metsulfuron-methyl is described in EP0318276.

According to an embodiment of the invention, the crystalline modification I of metsulfuron-methyl can be obtained by the processes below:

Metsulfuron-methyl in amorphous state is dissolved and then crystallized from solvents.

In one aspect, the present invention provides a process for preparing a crystalline modification I of metsulfuron-methyl comprising steps of:

i) dissolving metsulfuron-methyl in an amorphous state in a solvent;

ii) precipitating the dissolved compound into crystalline modification I of metsulfuron-methyl; and iii) isolating the precipitated crystalline modification I.

Suitable solvents for preparing metsulfuron-methyl crystalline modification I include: halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions having a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures thereof.

Preferred solvents include ethers, aromatic hydrocarbons (such as benzene, toluene, xylene, chlorobenzene), esters and aliphatic alcohols, and mixtures thereof. Particularly preferred solvents or solvent mixtures include isopropanol, toluene, methyl-tetrahydrofuran, diethyl carbonate, chlorobenzene, n-butyl acetate, isobutyl acetate, n-butanol, ethanol, ethyl malonate, methyl t-butyl ether, and mixtures thereof, particularly mixtures of toluene and butanol, mixtures of toluene and n-butyl acetate, mixtures of ethyl malonate and methyl t-butyl ether, as well as mixtures of butyl acetate and methyl t-butyl ether. Solvent mixtures of more than 2 components are also possible. In an embodiment of the present invention, solvents that include alcohols, such as methanol and ethanol, are highly preferred.

According to an embodiment of the present invention, crystalline modification I of metsulfuron-methyl is prepared by dissolving the amorphous metsulfuron-methyl in a solvent or a solvent mixture as a concentrated solution by heating from room temperature or ambient temperature to a temperature at or below the reflux temperature of the solvent or the solvent mixture. Preferably, the concentrated solutions can be prepared at the reflux temperature of the solvents. The concentration of the solution depends on the solubility of metsulfuron-methyl in the corresponding solvent or solvent mixture.

The concentrated homogeneous solution thus prepared as in step (i) is then cooled to room or ambient temperature or cooled to around 0° C. to 20° C. to crystallize the desired crystalline form from the solvent. The crystalline modification I of metsulfuron-methyl can also be crystallized out by concentrating the homogeneous solution by removing the solvent or solvent mixture to a certain volume, with or without applying vacuum, and below the reflux temperature of the solvent or the solvent mixture.

In another embodiment, crystallization of crystalline modification I of metsulfuron-methyl can also be obtained by adding seed crystals of the desired crystalline form during crystallization into a solution prepared in step (i), which can promote or accelerate the crystallization.

The seed crystal amount added to the concentrated solution is typically in the range of 0.001% to 10% by weight, more particularly in the range of 0.005% to 0.5% by weight, based on the weight of metsulfuron-methyl used for the preparation of concentrated solution in step (i). Preferably, the seed crystals are added to the concentrated solution at a temperature below the boiling point of the corresponding solvent or the solvent mixture.

Hence, the precipitation of the crystalline form I of metsulfuron-methyl can be effectively achieved from the concentrated solution by a skilled person.

The precipitated crystalline modification I of metsulfuron-methyl obtained from step (ii) is isolated by the usual solid component separating techniques from solutions, such as filtration, centrifugation or decantation. Then, the isolated solid will be washed with the same solvent or solvent mixture which was used for the preparation of concentrated solution in step (i). The washing is usually carried out using the corresponding solvent or solvent mixture between room temperature and 0° C. depending on the solubility of the crystal in order to avoid the loss of crystalline material in the corresponding washing solvent as much as possible.

The invention, in an embodiment, also relates to a composition comprising the crystalline modification I of metsulfuron-methyl. In a particular embodiment, the amount of the crystalline modification I of metsulfuron-methyl is less than 75% by weight of the composition, preferably less than 50% by weight of the composition, more preferably less than 30% by weight of the composition, still more preferably about 25% by weight of the composition.

The use of amorphous metsulfuron-methyl as a herbicide is known in the art and is used on a commercial scale. It has been found that the crystalline modification I of metsulfuron-methyl is also active in controlling weeds. As a result, the techniques of formulating and applying metsulfuron-methyl known in the art with respect to amorphous metsulfuron-methyl, for example as disclosed in the prior art documents discussed hereinbefore, can also be applied in an analogous manner to metsulfuron-methyl in the crystalline modification I of embodiments of the invention.

Accordingly, in a further aspect, the invention provides a herbicidal composition comprising metsulfuron-methyl in the crystalline modification I as defined hereinbefore.

Moreover, in yet another aspect, the invention additionally provides processes for preparing compositions for controlling weeds using the crystalline modification I of metsulfuron-methyl.

The crystalline modification I of metsulfuron-methyl can be included in a known manner in the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable auxiliaries, carriers and solvents.

In this context, the crystalline modification I of metsulfuron-methyl may be present in a concentration sufficient to achieve the required dosage when applied to plants or the loci thereof, desirably in a concentration of from about 0.1% to about 50% by weight of the total mixture. The formulations are prepared, for example, by extending the crystalline modification I of metsulfuron-methyl with water, solvents and carriers, using, if appropriate, emulsifiers and/or dispersants, and/or other auxiliaries.

These formulations are prepared by mixing the crystalline modification I of metsulfuron-methyl with customary auxiliaries, for example, one or more of liquid diluents, solid diluents, wetting agents, dispersants, thickening agents and other formulation ingredients.

Liquid diluents include, but are not limited to, water, N,N-dimethylmamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid diluents include, but are not limited to clays, synthetic and diatomaceous silicas, calcium and magnesium silicates, titanium dioxide, aluminum, calcium and zinc oxide, and mixtures thereof.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures thereof. Alkyl naphthalene sulphonates, sodium salts are particularly useful for the composition of the invention Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Ligninsulfonates such as sodium ligninsulfonates are particularly useful for the composition of the invention. Naphthalene sulfonate-formaldehyde condensates such as Naphthalenesulfonic acid, polymers with formaldehyde, and sodium salts are particularly useful for the composition of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose, and mixtures thereof. Synthetic thickening agents include derivatives of the former categories, and also polyvinyl alcohols, polyacrylamides, polyvinylpyrrolidones, various polyethers, their copolymers as well as polyacrylic acids and their salts, and mixtures thereof. Alkylpolyvinylpyrrolidones are particularly useful for the composition of the invention Other formulation ingredients can also be used in the present invention such as dyes, defoamers, drying agents, and the like. These ingredients are known to one skilled in the art.

The crystalline modification I of metsulfuron-methyl according to an embodiment of the invention can be present in formulations and in other forms that are prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals) or with agents for improving plant properties.

When used as herbicide, the crystalline modification I of metsulfuron-methyl according to an embodiment of the invention can furthermore be present in formulations and in other forms, prepared from these formulations, and as a mixture with inhibitors which reduce degradation of the active compounds after their use in the environment of the plant, on the surface of plant parts, or in plant tissues.

All plants and plant parts can be treated with the crystalline modification I of metsulfuron-methyl in accordance with an embodiment of the invention. In the present context, plants are to be understood as meaning all plants and plant populations, such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoots, leaves, needles, stalks, stems, flowers, fruit bodies, fruits, seeds, roots, tubers and rhizomes. Harvested materials, and vegetative and generative propagation materials, for example, cuttings, tubers, meristem tissues, rhizomes, offsets, seeds, single and multiple plant cells, and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown.

Treatment according to the invention of the plants and plant parts with the compositions or formulations of the inventions is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The benefits of embodiments of the invention are seen most when the herbicidal composition is applied to kill weeds in growing crops of useful plants: such as maize (corn) including field corns, pop corns and sweet corns, cotton, cereals, wheat, rice, oats, potatoes, sugar beets, plantation crops (such as bananas, fruit trees, rubber trees, tree nurseries), vines, Citrus, Olive, Amenity, asparagus, bushberries (such as blueberries), caneberries, cranberries, flax, grain sorghum, okra, peppermint, rhubarb, spearmint, turf grass, grapevine and sugarcane. In an embodiment of the invention, cereal is particularly suitable for treatment.

All percentages are given in weight % unless otherwise indicated.

Embodiments of the present invention will now be described by the following examples which are provided for illustrative purposes only, and not intended to limit the scope of the disclosure.

EXAMPLES

Example 1: Preparation of Amorphous Metsulfuron-Methyl in Accordance with the Disclosure of EP 0318276 A1

To an anhydrous suspension of 1.4 g of 2-amino-4-methoxy-6-methyl-1,3,5-triazine in 25 ml of methylene chloride is added with stirring at ambient temperature and pressure 2.4 g of 2-methoxycarbonylbenzenesulfonylisocyanate. The mixture is thereafter stirred for 16 hours and filtered. The filtrate is evaporated to dryness, the residue is triturated with butyl chloride and the product removed by filtration.

Figure 4:
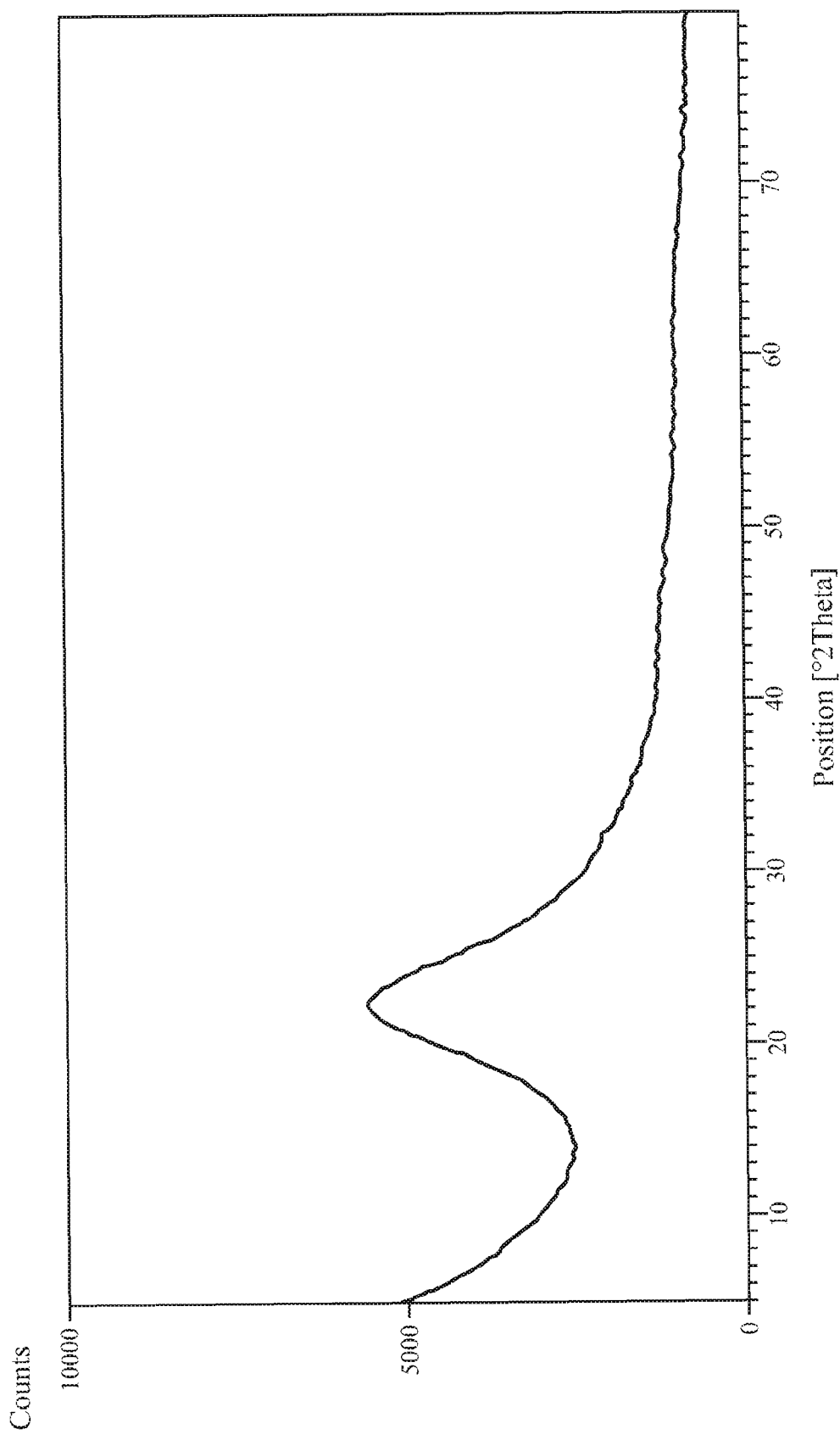
FIG. 4 is a graph showing the results of an X-ray powder diffractogram of amorphous metsulfuron-methyl.

As shown in FIG. 4, the X-ray powder diffraction pattern of the resulting metsulfuron-methyl product has no significant signals, which indicates the metsulfuron-methyl product prepared in accordance with the disclosure of EP 0318276 A1 is amorphous.

Preparation of Crystalline Modification I of Metsulfuron-Methyl

Example 2—Crystallization from Methanol

Metsulfuron-methyl sample prepared as described in Example 1 (10 g) was taken in a three-neck round bottom flask along with methanol (60 mL) and the resulting slurry was heated to 50° C. to obtain a homogeneous solution. The insoluble particles, if any, were filtered and the solution was slowly cooled to room temperature. Upon cooling, fine crystals were formed and the heterogeneous mixture was stirred at room temperature for 2 h. Then, the slurry was filtered and washed with methanol (3 mL). The filtered crystals were dried under vacuum at 60° C. in order to remove the methanol traces from the crystalline product. The crystalline product thus obtained had a purity of >98% and the recovered crystalline product as crystal was found to be not less than 80% yield.

The obtained crystal product was analyzed by IR, powder X-ray and DSC analyses and found to be crystalline modification I of metsulfuron-methyl as shown in FIGS. 1, 2 and 3, respectively.

The differential scanning calorimetry (DSC) thermogram (FIG. 3) shows an endothermic melting peak with onset at 170.5° C. and peak maximum at 173.6° C.

The IR spectrum of metsulfuron-methyl shows the functional group characteristic vibrations at 3076.92, 2952.03, 2160.21, 2022.83, 1726.29 and 1702.52 cm$^{-1}$ as shown in FIG. 1.

The powder X-ray diffractogram of crystals showed the reflexes as shown in FIG. 2 and the values are summarized in Table 1.

TABLE 1

Crystal Form A

| 2 θ (°) | d (Å) |
|---|---|
| 6.28 ± 0.2 | 14.07 ± 0.05 |
| 12.61 ± 0.2 | 7.02 ± 0.05 |
| 13.50 ± 0.2 | 6.56 ± 0.05 |
| 16.59 ± 0.2 | 5.34 ± 0.05 |
| 17.66 ± 0.2 | 5.02 ± 0.05 |
| 19.70 ± 0.2 | 4.51 ± 0.05 |
| 21.63 ± 0.2 | 4.32 ± 0.05 |
| 21.84 ± 0.2 | 4.11 ± 0.05 |
| 23.22 ± 0.2 | 4.07 ± 0.05 |
| 24.21 ± 0.2 | 3.83 ± 0.05 |
| 27.25 ± 0.2 | 3.27 ± 0.05 |
| 27.98 ± 0.2 | 3.19 ± 0.05 |
| 29.25 ± 0.2 | 3.05 ± 0.05 |

Table 1. Powder X-Ray Diffractogram Reflexes of Crystalline Modification I of Metsulfuron-Methyl Example 3—Crystallization from Ethanol Metsulfuron-methyl (5 g) sample prepared in Example 1 was taken in a three-neck round bottom flask along with ethanol (35 mL) and the resulting slurry was heated to 60° C. to get a homogeneous solution. The resultant hot solution was filtered to remove the insoluble (if any) and the solution was slowly cooled to ambient temperature. Product was precipitated out as fine crystal during cooling and the mixture was stirred at room temperature for 2 h. Then, the slurry was filtered, washed with ethanol (3 mL) and dried under vacuum at room temperature in order to remove the ethanol traces from the crystal. The crystal thus obtained had a purity of >98% and the recovered yield was found to be not less than 80%.

The crystals were characterized as being metsulfuron-methyl crystalline modification I using infra-red spectrometry, X-ray diffraction and DSC, as described in Example 2.

Example 4: Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Metsulfuron-methyl, crystalline modification I, 98% (prepared in Example 2) | 40.8 | 0 | Active compound |
| Amorphous metsulfuron-methyl (prepared in Example 1) | 0 | 40.8 | Active compound |
| Sodium lignosulfonate (REAX ® 88B) | 22 | 22 | Dispersing agent |
| Alkylpolyvinylpynolidone | 20 | 20 | Thickening agent |
| Corn oil | Balance to 100% | Balance to 100% | Carrier |

Example 5: Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Metsulfuron-methyl, crystalline modification I, 98% (prepared in Example 2) | 25.51 | 0 | Active compound |
| Amorphous metsulfuron-methyl (prepared in Example 1) | 0 | 25.51 | Active compound |
| Lignosulfonic acid, sodium salt, (REAX ® 88B) | 15 | 15 | Dispersing agent |
| Naphthalenesulfonic acid, polymer with formaldehyde, sodium salt (TAMOL ® NN 8906) | 6 | 6 | Dispersing agent |
| Sodium acetate | 4 | 4 | Filler |
| Sodium carbonate | 4 | 4 | Filler |
| Non-ionic aqueous emulsion of Polydimethylsiloxanes | 1 | 1 | Antifoaming agent |
| Mannitol | Balance to 100% | Balance to 100% | carrier |

Example 6: Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Metsulfuron-methyl, crystalline modification I, 98% (prepared in Example 2) | 25.51 | 0 | Active compound |
| Amorphous metsulfuron-methyl (prepared in Example 1) | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Sucrose | 10 | 10 | Filler |
| Non-ionic aqueous emulsion of Polydimethylsiloxanes | 1 | 1 | Antifoaming agent |
| Mannitol | Balance to 100% | Balance to 100% | Carrier |

Example 7: Determining Water Solubility

A stock pH 7 buffer solution was prepared by adding aqueous sodium hydroxide solution (0.1 M, 145 mL) to aqueous potassium dihydrogen phosphate solution (0.1 M, 250 mL), and then adding sufficient distilled water to adjust the final volume to 500 mL. At least 1 time and up to about 5 times the amount of metsulfuron-methyl needed for saturation was added to a mixing vessel containing stock buffer solution at the test temperature (e.g., 20° C.). The mixture was magnetically stirred in the dark while being maintained at the test temperature. Samples were periodically removed for analysis. The samples were centrifuged using a high speed, temperature-controlled centrifuge at the test temperature for about 20 minutes at >12000 G to remove suspended particles. An aliquot of each supernatant was taken for analysis.

The concentration of metsulfuron-methyl in the supernatant was determined by a high pressure liquid chromatography (HPLC) with a reversed phase chromatography column and UV detection. The method should include development of best-fit calibration curves based on at least three standards using linear regression analysis Samples were successively withdrawn from the mixing vessel and analyzed until three successive samples show little or no variation in concentration. The test is preferably replicated to ensure accuracy.

TABLE 5

| Sample | Formulation | Original concentration, % | Concentration measured by HPLC after treatment, % | Solubility |
|---|---|---|---|---|
| Metsulfuron-methyl, crystalline modification I, 98% (prepared in Example 2) | OD | 40 | 35 | 88% |
| Amorphous metsulfuron-methyl (prepared in Example 1) | OD | 40 | 14 | 35% |
| Metsulfuron-methyl, crystalline modification I, 98% (prepared in Example 2) | SG | 25 | 24.9 | 99.6% |
| Amorphous metsulfuron-methyl (prepared in Example 1) | SG | 25 | 15 | 60% |
| Metsulfuron-methyl, crystalline modification I, 98% (prepared in Example 2) | WG | 25 | 23 | 92% |
| Amorphous metsulfuron-methyl (prepared in Example 1) | WG | 25 | 12 | 48% |

Example 8: Cleanout Test

The test was conducted by dispersing in water a sample to produce a concentration that is normally used when applying the herbicide: 25% metsulfuron-methyl. The sample was added to tap water (300 mL) in a 400 mL beaker and magnetically stirred for 2 minutes. The mixture was then stirred for 2 minutes, whereupon the resulting dispersion was dispensed in three 100 mL aliquots to 4-oz (118 mL) polyethylene bottles. The bottles were capped, inverted twice and allowed to stand overnight.

After standing overnight, each individual bottle was inverted twice and the liquid contents were then poured out. Tap water (10 mL) was added and the bottle was inverted until all sediment was re-suspended, whereupon the contents were poured out. Tap water (100 mL) was added and the bottle was inverted twice and then allowed to stand undisturbed for 10 minutes. The bottle was inverted twice more and the contents were poured out. Acetonitrile (10 mL) was added to the bottle to extract any remaining material. The acetonitrile solution was analyzed by reversed-phase liquid chromatography with UV detection. The cleanout rating (the concentration of metsulfuron-methyl herbicide in the acetonitrile solution) is reported in % in Table 6 below. Lower cleanout ratings indicate more effective cleanout compared to higher ratings.

TABLE 6

| Sample | Formulation | Cleanout rating, % |
|---|---|---|
| Metsulfuron-methyl, crystalline modification I, 98% (prepared in Example 2) | OD | 5 |
| Amorphous metsulfuron-methyl, prepared in Example 1 | OD | 26 |
| Metsulfuron-methyl, crystalline modification I, 98% (prepared in Example 2) | SG | 0.1 |
| Amorphous metsulfuron-methyl, prepared in Example 1 | SG | 10 |
| Metsulfuron-methyl, crystalline modification I, 98% (prepared in Example 2) | WG | 2 |
| Amorphous metsulfuron-methyl (prepared in Example 1) | WG | 13 |

Although methanol and ethanol are exemplified above as solvents to produce crystalline modification I of metsulfuron-methyl, other solvents disclosed herein are also suitable for producing this crystalline modification using the procedures described herein, or such modifications thereof as would be apparent to one of ordinary skill in this art in possession of the above disclosure.

The invention claimed is:

1. A crystalline modification I of metsulfuron-methyl (methyl 2-[[[[(4-methoxy-6-methyl-1,3,5-triazin-2-yl)amino]carbonyl]amino]sulfonyl]benzoate) obtained by (i) dissolving metsulfuron-methyl in an amorphous state into at least one of methanol or ethanol to create a slurry, (ii) heating the slurry to prepare a homogeneous solution, (iii) filtering the homogeneous solution to remove any insoluble particles, (iv) cooling the solution to form crystals, (v) mixing the cooled crystalline solution, (vi) filtering the crystalline solution to obtain filtered crystals, (vii) washing the filtered crystals with said at least one of methanol or ethanol, and (viii) drying the washed crystals under vacuum, wherein the obtained crystalline modification I of metsulfuron-methyl exhibiting each of the following reflexes as 2θ values in X-ray powder diffractogram recorded using Cu-Kα radiation at 25° C.:

$$2\theta = 6.28 \pm 0.2 \tag{1}$$

$$2\theta = 12.61 \pm 0.2 \tag{2}$$

$$2\theta = 13.50 \pm 0.2 \tag{3}$$

$$2\theta = 16.59 \pm 0.2 \tag{4}$$

$$2\theta = 17.66 \pm 0.2 \tag{5}$$

$$2\theta = 19.70 \pm 0.2 \tag{6}$$

$$2\theta = 21.63 \pm 0.2 \tag{7}$$

$$2\theta = 21.84 \pm 0.2 \tag{8}$$

$$2\theta = 23.22 \pm 0.2 \tag{9}$$

$$2\theta = 24.21 \pm 0.2 \tag{10}$$

$$2\theta = 27.25 \pm 0.2 \tag{11}$$

$$2\theta = 27.98 \pm 0.2 \tag{12}, \text{and}$$

$$2\theta = 29.25 \pm 0.2 \tag{13}; \text{and}$$

wherein the crystalline modification I of metsulfuron-methyl exhibits a Differential Scanning Calorimeter (DSC) thermogram having an endothermic melting peak with onset at 170.5° C. and peak maximum at 173.6° C.

2. The crystalline modification I of metsulfuron-methyl exhibiting an IR spectrum with the following bands at 3076.92, 2952.03, 2160.21, 2022.83, 1726.29 and 1702.52 $cm^{-1}$.

3. A crystalline modification I of metsulfuron-methyl according to claim 1, wherein said step iv) comprises cooling the solution to ambient temperature or to around 0° C. to 20° C.

4. A crystalline material comprising a crystalline modification I of metsulfuron-methyl obtained according to claim 1 and having a content of crystalline modification I of metsulfuron-methyl content of at least 90% by weight.

5. A composition comprising the crystalline modification I of metsulfuron-methyl according to claim 1 and at least one auxiliary.

6. The composition according to claim 5, wherein the auxiliary is selected from the group consisting of a surfactant, a thickening agent, an antifreeze agent, a biocide, an adjuvant, and mixtures thereof.

7. The composition according to claim 5, in form of a suspension concentrate, an oil-based suspension concentrate, a soluble granule, a dispersible concentrate, an emulsifiable concentrate, an emulsion concentrate, an emulsion seed dressing, a suspension seed dressing, a granule, a microgranule, a suspoemulsion, and a water-dispersible granule.

8. The composition according to claim 5, in form of a water-dispersible granule, a soluble granule or an oil-based suspension concentrates.

9. A crystalline modification I of metsulfuron-methyl according to claim 3, wherein said step iv) includes adding a seed crystal of the crystalline modification I while cooling the solution.

\* \* \* \* \*